United States Patent
Foster et al.

(10) Patent No.: US 11,964,256 B2
(45) Date of Patent: Apr. 23, 2024

(54) FCC CATALYST ADDITIVE WITH MIXED ALUMINA

(71) Applicant: Ketjen Limited Liability Company, Houston, TX (US)

(72) Inventors: Edward Lee Foster, Pearland, TX (US); Maria Margaret Ludvig, El Lago, TX (US); Kevin Alfonso Miller, League City, TX (US)

(73) Assignee: Ketjen Limited Liability Company, Houston, TX (US)

( * ) Notice: Subject to any disclaimer, the term of this patent is extended or adjusted under 35 U.S.C. 154(b) by 1055 days.

(21) Appl. No.: 16/494,875

(22) PCT Filed: Mar. 16, 2018

(86) PCT No.: PCT/US2018/022967
§ 371 (c)(1),
(2) Date: Sep. 17, 2019

(87) PCT Pub. No.: WO2018/170452
PCT Pub. Date: Sep. 20, 2018

(65) Prior Publication Data
US 2023/0149905 A1 May 18, 2023

Related U.S. Application Data

(60) Provisional application No. 62/472,980, filed on Mar. 17, 2017.

(51) Int. Cl.
| | |
|---|---|
| *B01J 29/06* | (2006.01) |
| *B01J 21/12* | (2006.01) |
| *B01J 21/16* | (2006.01) |
| *B01J 29/40* | (2006.01) |
| *B01J 29/70* | (2006.01) |
| *B01J 35/00* | (2006.01) |
| *C07C 4/06* | (2006.01) |

(52) U.S. Cl.
CPC .............. *B01J 21/12* (2013.01); *B01J 21/16* (2013.01); *B01J 29/40* (2013.01); *B01J 29/70* (2013.01); *B01J 35/002* (2013.01); *C07C 4/06* (2013.01); *C07C 2521/12* (2013.01); *C07C 2521/16* (2013.01); *C07C 2529/40* (2013.01); *C07C 2529/70* (2013.01)

(58) Field of Classification Search
CPC ... B01J 21/12; B01J 21/16; B01J 29/40; B01J 29/70; B01J 29/7007; B01J 29/7034; B01J 29/7038; B01J 2229/42; B01J 35/002; B01J 35/0006; B01J 35/023; B01J 37/28; C07C 4/06; C07C 2521/12; C07C 2521/16; C07C 2529/40; C07C 2529/70; C07C 2529/06
USPC ...... 502/60, 63, 64, 68, 69, 71, 77
See application file for complete search history.

(56) References Cited

U.S. PATENT DOCUMENTS

| | | |
|---|---|---|
| 3,758,403 A | 9/1973 | Rosinski et al. |
| 5,456,821 A | 10/1995 | Absil et al. |
| 5,472,594 A | 12/1995 | Tsang et al. |
| 5,521,133 A | 5/1996 | Koermer et al. |
| 6,048,577 A | 4/2000 | Garg |
| 6,080,303 A | 6/2000 | Cao et al. |
| 6,211,104 B1 | 4/2001 | Shi et al. |
| 6,558,647 B2 | 5/2003 | Lacombe et al. |
| 6,916,757 B2 | 7/2005 | Ziebarth et al. |
| 7,375,048 B2 | 5/2008 | Smith et al. |
| 7,459,413 B2 | 12/2008 | Shen et al. |
| 7,547,813 B2 * | 6/2009 | Smith ................ C10G 11/05 585/653 |
| 7,727,924 B2 | 6/2010 | Liu et al. |
| 8,178,740 B2 | 5/2012 | Nicholas et al. |
| 8,658,024 B2 | 2/2014 | Long et al. |
| 8,791,280 B2 | 7/2014 | Rizkalla |
| 10,799,855 B2 | 10/2020 | Gao et al. |
| 10,888,852 B2 | 1/2021 | Ludvig et al. |
| 2007/0274903 A1 * | 11/2007 | Laheij ............... C04B 35/62605 423/625 |
| 2013/0013141 A1 | 5/2013 | Buchanan et al. |
| 2013/0131419 A1 | 5/2013 | Buchanan et al. |
| 2014/0206526 A1 | 7/2014 | Gao et al. |
| 2015/0045208 A1 | 2/2015 | Adkins et al. |
| 2016/0074842 A1 * | 3/2016 | Sarkar ............... B01J 35/1061 208/114 |
| 2017/0144140 A1 * | 5/2017 | Sarkar ............... B01J 37/0045 |

FOREIGN PATENT DOCUMENTS

| | | |
|---|---|---|
| EP | 5511013 | 4/1992 |
| JP | 2011088137 A | 5/2011 |
| NL | 9301333 | 7/1993 |
| WO | 1994/013754 | 6/1994 |
| WO | 1998/041595 | 9/1998 |
| WO | WO 2022/072544 | * 4/2022 |

OTHER PUBLICATIONS

Karagedov et al., "Preparation and sintering pure nanocrystalline alpha-alumina powder", Journal of the European Ceramic Society, 32 (2012), 219-225.*

(Continued)

*Primary Examiner* — Elizabeth D Wood

(57) ABSTRACT

Provided is a Fluid Catalytic Cracking catalyst additive composition and method of making the same. The catalyst additive composition comprises zeolite about 35 wt % to about 80 wt %, preferably about 40 wt % to about 70 wt %; silica about 0 wt % to about 10 wt %, preferably about 2 wt % to about 10 wt %; about 10.5 wt % to 20 wt % alumina and about 7 wt % to 20 wt % $P_2O_5$, preferably about 11 wt % to about 18 wt %, and the balance clay which can fall between 0 and 50 wt %. The alumina is typically derived from more than one source, such as at least an amorphous or small crystallite size pseudo-boehmite alumina and then either a large crystallite size alumina or other reactive alumina.

14 Claims, No Drawings

(56) References Cited

OTHER PUBLICATIONS

Gurel et al., Reactive alumina production for the refractory industry, Powder Technology 196 (2009), 115-121.*

PCT/US2018/022967 International Search Report and Written Opinion of the International Searching Authority, Date Mailed: Jun. 22, 2018.

PCT/US2018/022967 International Preliminary Report on Patentability of the International Searching Authority, Date of Issuance: Sep. 17, 2019.

* cited by examiner

FCC CATALYST ADDITIVE WITH MIXED ALUMINA

TECHNICAL FIELD

This invention relates to a Fluid Catalytic Cracking (FCC) material with mixed alumina. More particularly, the present invention relates to a zeolite based FCC additive and a method for preparing the same.

BACKGROUND

One of the most preferred methods to convert heavy hydrocarbon feed stocks to lighter products, such as gasoline and distillate range fractions is fluid catalytic cracking (FCC). There is, however, an increasing need to enhance the yield of lower olefins, LPG propylene and other light olefin yields ($C_2$-$C_4$ hydrocarbon) in the product slate from catalytic cracking processes. In FCC practice, there are two ways to increase light olefin selectivity. The first of these is to increase the reaction temperature. This will increase the contribution of thermal cracking, which leads to increased formation of lighter products. For instance, in the so-called DCC (Deep Catalytic Cracking) process, a specific type of FCC process, higher temperatures and increased amounts of steam are used. However, thermal cracking is not very selective and produces large amounts of products of relatively little value, such as hydrogen, methane, ethane, and ethylene, in the "wet gas" (which contains $H_2$ and $C_1$-$C_4$ products). Wet gas compression often limits refinery operation.

The second method is to add an olefin-selective, zeolite-containing additive such as a ZSM-5-containing additive. Conventional additives usually contain phosphorus-activated ZSM-5, which selectively converts primary cracking products (e.g., gasoline olefins) to $C_3$ and $C_4$ olefins. Improvement of the activity or the selectivity with phosphorus is known to increase the effectiveness of ZSM-5. For instance, EP-A-511 013 describes the treatment of ZSM-5 with phosphorus to increase the propylene selectivity. Further, U.S. Pat. No. 5,472,594 describes a process for converting a hydrocarbon feed to a product containing improved yields of $C_4$/$C_5$ olefins with a catalyst composition containing zeolite Y and an additive comprising a phosphorus-containing medium pore zeolite such as ZSM-5. Also Mobil's WO 98/41595 describes a process for the catalytic cracking of a hydrocarbon feedstock to produce an enhanced yield of $C_3$ to $C_5$ olefins using a catalyst composition comprising a large pore molecular sieve such as zeolite Y and an additive comprising a phosphorus-containing ZSM-5 blended in with the base catalyst containing zeolite Y. The same is described in U.S. Pat. No. 5,456,821. WO 94/13754 describes the same process using a catalyst composition containing a large pore molecular sieve and an additive containing a specific ZSM-5 which optionally contains 1.5 to 5.5 wt % elemental phosphorus. Also U.S. Pat. No. 5,521,133 describes the preparation of a ZSM-5 additive by injecting a ZSM-5 and kaolin slurry with phosphoric acid prior to spray-drying.

Zeolites are one of the most widely used catalytic materials in hydrocarbon conversions. It is being widely used as catalyst and/or additive in catalytic crackers or incorporated in cracking catalysts. The use of cracking catalyst comprised of a large pore size crystalline zeolite (pore size greater than 7 angstrom units) in admixture with ZSM-5 type zeolite for improving the octane number has been reported in U.S. Pat. No. 3,758,403. When a conventional catalyst containing 10 percent REY is added with ZSM-5 molecular sieve in the range of 1.5 percent to 10 percent, the gasoline octane number and the yield of lower olefins are increased. However, it has been found that the efficacy is reduced with increasing amount of ZSM-5 molecular sieve. Using an additive that contains ZSM-5 molecular sieve has the same effect.

In order to increase the production of light olefins and to increase the selectivity towards propylene, it has been attempted to increase the amount of zeolite, such as ZSM-5, in the catalyst system. This can either be done by increasing the amount of zeolite within the additive or to increase the amount of additive that is blended in with the base FCC catalyst. Both approaches have their drawbacks. Increasing the blend of the additive comes at the cost of the amount of the base catalyst and decreases cracking. Increasing zeolite crystal within the additive has been known to cause problems with certain physical attributes of the additive. In particular, as the amount of zeolite crystal is added, binding effect goes down, and there is an increased amount of attrition.

One example at increasing zeolite content in the additive is in U.S. Pat. No. 6,916,757. The invention of the '757 patent is described as having an additive comprising about 30 to about 85% zeolite and a binder system components comprising greater than 9 to about 24% by weight phosphorus, measured as $P_2O_5$ based on the weight of the total additive and added alumina in an amount ranging from about 5 to about 10% by weight of the total additive; said additive further having a molar ratio of phosphorus to total alumina of at least 0.2 to about 1.9. Added alumina is defined as alumina separately added to the slurry of starting components and dispersed in the matrix of the catalyst. The amount of added alumina is taught to be lower than 10% and the examples are said to "illustrate the advantage of catalysts comprising about 10% or less added alumina."

Another prior art example is U.S. Pat. No. 7,375,048. The '048 invention is described as a catalyst comprising (a) at least about 30% by weight of an intermediate pore size zeolite, (b) about 3-15% by weight phosphorus, measured as $P_2O_5$, (c) about 15 to 45 wt. % kaolin, and (d) an unreactive metal component other than kaolin with a BET surface area of less than 50 $m^2$/g, wherein said unreactive metal component is alpha-alumina. Generally, the patent describes the unreactive alumina component being in amounts ranging from 3-25 weight %, more typically from about 4-10% by weight. The '048 patent also teaches optionally to add a reactive alumina component. This component can be in the amount of 2-20%, but typically in an amount of 4-8%. The total weight of alumina, reactive or unreactive, ranges from at least 5 wt. % and typically will range from about 8-25 wt. %. The '048 patent further finds that the amount of alumina in the form of added unreactive and reactive alumina, in amounts of greater than 10%, have been found most useful, including amounts of from about 12-20 wt. %.

Therefore there exists a need for a high zeolite FCC additive with acceptable physicals that allow the additive to perform at a constant or an improved level.

SUMMARY OF THE INVENTION

The present invention relates to a catalytic material specifically meant to be employed in the process for cracking, a hydrocarbon feed over a particular catalyst composition to produce conversion product hydrocarbon compounds of lower molecular weight than feed hydrocarbons, e.g., product comprising a high propylene fraction and increased LPG.

A typical FCC additive procedure is as follows. Alumina and/or silica binder is mixed with required amount of zeolite slurry, clay, and phosphoric acid. This mixture is sent to a spray dryer to make the final catalyst. The alumina and/or silica binder is added to the catalyst mixture for performance and good physical properties, mainly ABD and attrition resistance of the FCC additive. The alumina binder can be an amorphous, boehmite, gibbsite, bayerite, alumina sols or pseudo-boehmite alumina sol or other suitable reactive alumina (particle size <3000 nm) either mechanically or chemically dispersed or dissolved with the use of monoprotic acids, like $HNO_3$, HCl, formic or any other aluminum source dissolved in monoprotic acid or optionally a creation of a sol type material with other acids, one example being $H_3PO_4$. The silica binder can be sources of silica in suitable dispersed form and include silica hydrosol, silica gel, silica sol and silicic acid.

The present invention, however, is based on manufacturing additives with combinations of two or more reactive alumina towards phosphoric acid (e.g., >10.5 wt % total alumina added to the mixture). Typically, at least one alumina is an amorphous or small crystallite size alumina and the other is a large crystallite size boehmite type alumina or other reactive type alumina with structure other than boehmite, such as gibbsite or bayerite. The aluminas are dispersed or peptized with any suitable acid, by known mechanical means, or by chemical reaction or may be self-dispersing to particle size <3000 nm. Crystallite size used throughout this disclosure is to be understood as average crystallite size.

In accordance with the present invention there is provided a zeolite based hydrothermally resistant FCC catalyst additive which comprises: zeolite about 35 wt % to about 80 wt %; silica about 0 wt % to about 10 wt %; about 10.5 wt % to 20 wt % alumina and about 7 wt % to 20 wt % $P_2O_5$ and the balance clay which can fall between 0 and 50 wt %. Using the general knowledge of one skilled in the art, the total amount of the various components can be maximized for performance within the above stated ranges.

In still another aspect of the present invention there is provided a process for preparation of a zeolite based FCC catalyst additive that selectively improves the yield of propylene. A process of the present invention is also aimed at providing a FCC additive catalyst that is capable of providing and sustaining a high propylene yield for an extended time period.

These and still other embodiments, advantages and features of the present invention shall become further apparent from the following detailed description, including the appended claims.

DETAILED DESCRIPTION OF THE INVENTION

Unless otherwise indicated, weight percent (%) as used herein is the dry base weight percent of the specified form of the substance, based upon the total dry base weight of the product for which the specified substance or form of substance is a constituent or component. It should further be understood that, when describing steps or components or elements as being preferred in some manner herein, they are preferred as of the initial date of this disclosure, and that such preference(s) could of course vary depending upon a given circumstance or future development in the art.

The catalyst additive of the present invention is typically prepared by the following process:
(a) dose alumina and water (or suitable aqueous solution) to tank to form an alumina slurry;
(b) chemically or mechanically disperse or peptize alumina, if necessary to particle size 3000 nm;
(c) dose to the alumina slurry the balance of other ingredients, including zeolite source, silica source, phosphorous source, clay, and optionally additional alumina sources;
(d) send the slurry to a spray dryer;
(e) collect spray dried catalyst powder and this is the final additive;
(f) optionally, the final product can be calcined, for example at a temperature of between about 250° C. and about 700° C.

For purposes of this invention, the reactive alumina mentioned in step (a) and (c) is typically at least an amorphous or small crystallite size pseudo-boehmite alumina and then either a either a large crystallite size alumina or other reactive alumina. The alumina added in the present invention is a mixture of more than one alumina source. The alumina is generally considered to be reactive when mixed with a phosphorous source.

The first potential source of alumina is what is identified as amorphous or small crystallite size pseudo-boehmite alumina or "small crystallite alumina" ("SCA"). These small crystallite aluminas typically have crystallite size generally less than about 10 nm. Examples of small crystallite size aluminas include pseudo-boehmite or alumina sols, such as aluminum chlorohydrol and aluminum nitrate nonhydrate.

The second source of alumina is either what is identified as "large crystallite alumina" ("LCA") or other reactive alumina with structure other than boehmite. Large crystallite aluminas typically have crystallite size generally greater than about 10 nm, and preferably greater than about 15 nm. The preferred range of crystallite size is about 25 nm or larger. Examples of suitable large crystallite alumina include boehmite sources. In addition to the LCA described above, the second source of alumina may be non-boehmite sources, but still reactive with phosphorus, such as gibbsite and bayerite.

The total amount of alumina added in step (a) and/or (c) is typically in the range of about 10.5 wt % to about 20.0 wt % of the final dried additive, calculated as $Al_2O_3$, and preferably between about 11.5 wt % and about 15 wt %. This alumina content is separate from the alumina that may be measured in other components, such as the zeolite or the clay and is derived from the alumina added at these steps. It is preferable that a mixture of two or more alumina sources is used. It is preferable that one source have a lower crystallite size than the other. In one embodiment, the total amount of lower crystallite size alumina is typically in the range of 2.5 wt % to about 15 wt %. And the amount of the larger crystallite size alumina would typically be in the amount of about 0 wt % to about 10 wt %. The total amount of alumina remains the same as above, typically in the range of about 10.5 wt % to about 20.0 wt %.

During the above step (b), an acid is added to disperse or peptize the alumina, if necessary. Suitable acids include formic acid, nitric acid, phosphinic acid, acetic, hydrochloric, methanesulfonic, methanesulphamic or other known dispersing acids. The alumina may also be dispersed by any known physical or mechanical means or may be self-dispersing. Alternatively, acids may be added to create a sol type material.

During the above step (c), any suitable phosphorus-containing compound, i.e. any phosphorus-containing compound having a covalent or ionic constituent capable of reacting with hydrogen ion, may be employed, for example phosphoric acid and its salts such as ammonium dihydrogen phosphate and diammonium hydrogen phosphate, ammonium hypophosphate, ammonium orthophosphate, ammonium dihydrogen orthophosphate, ammonium hydrogen orthophosphate, triammonium phosphate, phosphines, and phosphites. Suitable phosphorus-containing compounds include derivatives of groups represented. by $PX_3$, $RPX_2$, $R_2PX$, RIP, $R_3P=O$, $RPO_2$, $RPO(OX)_2$, $PO(OX)_3$, $R_2P(O)OX$, $RP(OX)_2$, $ROP(OX)_2$, and $(RO)_2POP(OR)_2$, wherein R is an alkyl or phenyl radical and X is hydrogen, R or halide. These compounds include primary, $RPH_2$, secondary, $R_2PH$, and tertiary, $R_3P$, phosphines such as butyl phosphine; tertiary phosphine oxides, $R_3PO$, such as tributyl phosphine; primary, $RP(O)(OX)_2$, and secondary, $R_2P(O)OX$, phosphonic acids such as benzene phosphonic acid; esters of the phosphonic acids such as diethyl phosphonate, $(RO)_2P(O)H$, dialkyl phosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as monopropyl ester, alkyl-dialkyl phosphinites, $(RO)P_2$, and dialkyl phosphonite, $(RO)_2$ PR esters. Examples of phosphite esters include trimethyl phosphite, triethyl phosphite, diisopropyl phosphite, butyl phosphite; and pyrophosphites such as tetrapyrophosphate. The alkyl groups in the mentioned compounds contain 1 to 4 carbon atoms. Other suitable phosphorus-containing compounds include phosphorus halides such as phosphorus trichloride, bromide, and iodide, alkyl phosphorodichloridites, $(RO)PCl_2$, dialkyl phosphorochloridites, $(RO)_2PCl$, alkyl phosphonochloridates, $(RO)(R)P(O)Cl$, and dialkyl phosphinochloridates, $R_2P(O)Cl$.

The amount of phosphorous added during step (c) is preferably about 11 wt % to about 18 wt % $P_2O_5$ but within the range of about 7 wt % to about 20 wt % $P_2O_5$ on catalyst, by dry weight basis.

The zeolite added during step (c) is a typical olefin-selective zeolites, which is defined as a zeolite having a silica/alumina ratio above 10, preferably above 15, and up to 12 rings. Typically, the amount of zeolite added to the mixture is about 35 wt % to about 80 wt %, preferably about 40 wt % to about 70 wt %.

Examples of suitable olefin-selective zeolites are MFI-type zeolites, MEL-type zeolites such as ZSM-11, MTW-type zeolites such as ZSM-12, MWW-type zeolites such as MCM-22, MCM-36, MCM-49, MCM-56, BEA-type zeolites such as zeolite beta, ZSM-35 and ZSM-22. MFI-type zeolites are preferred. MFI-type zeolites are as defined in the ATLAS OF ZEOLITE STRUCTURE TYPES, W. M. Meier and D. H. Olson, 3rd revised edition (1992), Butterworth-Heinemann, and include ZSM-5, ST-5, ZSM-8, ZSM-11, silicalite, LZ-105, LZ-222, LZ-223, LZ-241, LZ-269, L2-242, AMS-1B, AZ-1, BOR-C, Boralite, Encilite, FZ-1, NU-4, NU-5; T5-1, TSZ, TSZ-III, TZ01, TZ, USC-4, USI-108, ZBH, ZB-11, ZBM-30, ZKQ-1B, ZMQ-TB. It should be noted that the ZRP zeolite as described in NL 9301333 is not considered a MH-type zeolite within the context of this description.

Further during step (c), it is typical to add a silica binder in the range of about 0 wt % to about 15 wt %. More preferably about 2 wt % to about 10 wt % silica binder is added to the slurry for optimal binding and performance. Sources of silica in a suitably dispersed form include silica hydrosol, silica gel, silica sol, and silicic acid. The preferred source of silica is an aqueous colloidal dispersion of silica particles. Silica sols suitable for use in the present invention are any of those derived from an ion-exchange process or other means which have a substantially uniform particle size within the range of about 10 to about 2000 Angstroms.

The balance of the additive is clays, such as kaolin, bentonite, or meta-kaolin, or other fillers. This would include any suitable non-zeolitic inorganic oxide materials and other clays like halloysite or attapulgite as well.

As previously noted, the resulting catalyst additive typically comprises zeolite about 35 wt % to about 80 wt %, preferably about 40 wt to about 70 wt; silica about 0 wt % to about 10 wt %, preferably about 2 wt % to about 10 wt %; about 10.5 wt % to 20 wt % alumina and about 7 wt % to 20 wt % $P_2O_5$, preferably about 11 wt % to about 18 wt %, and the balance clay which can fall between 0 and 50 wt %. The alumina is typically derived from more than one source, such as at least an amorphous or small crystallite size pseudo-boehmite alumina and then either a either a large crystallite size alumina or other reactive alumina, as discussed above.

Compositions according to this invention can be added to an FCC unit with the hydrocarbon feed, simultaneously with one or more catalysts, or after the hydrocarbon feed and one or more catalysts have been added. In one embodiment, composition according to this invention is combined with one or more FCC catalysts. Said catalyst composition can suitably be used in the catalytic cracking of hydrocarbon feedstocks and has high efficiency in the production of light olefins while maintaining the bottoms conversion. The catalyst composition may also be used in the so-called. DCC process even when using lower temperatures than usual in DCC processes. The material may also be useful in HSFCC and Naphtha conversion processes.

EXAMPLES

The invention is illustrated in the following non-limiting examples, which are provided for the purpose of representation, and are not to be construed as limiting the scope of the invention.

Prior to any lab testing the catalyst must be deactivated to simulate catalyst in a refinery unit, this is typically done with steam. These samples were deactivated either by cyclic deactivation with MN which consists of cracking, stripping and regeneration steps in the presence of steam or with 100% steam at higher temperatures, which are industrially accepted deactivation methods for FCC catalysts. The deactivation step is known in the art, and is necessary to catalytic activity. In commercial FCC setting, deactivation occurs shortly after catalyst introduction, and does not need to be carried out as a separate step. The Fluid microactivity test, or Fluidized-bed Simulation Test (FST) or Advanced Cracking Evaluation (ACE) is a test known and generally accepted in the art for ascertaining the FCC cracking activity of a catalyst. In ACE the test is conducted with a series of four catalyst-to-feed ratios (CTO) which are obtained by varying the mass of feed injected to the reactor, while using the same amount of catalyst for all runs. The testing apparatus simulates the cracking of a known amount of a hydrocarbon feedstock of known amount and compositional characteristics. This small scale testing unit is a once through unit and operated approximately as in ASTM 5154-10. For testing additives, one blends it with an FCC catalyst prior to performance testing at concentrations to simulate commercial use. For the following examples, additives were blended at 5% blends. Attrition Index (AI) was measured using a modified ASTM procedure.

The examples below utilize a typical VGO crude oil. Other feeds can be used and the feed properties do impact the absolute yields of LPG and in particular propylene.

Background Comparative. In order to compare the cumulative effect and benefits of the present inventions, two presently available commercial products were used as comparatives. The first product is a 40% zeolite additive and the other is a 50% zeolite additive. The 40% additive (A-when subjected to the above tests, show a 0.70 ABD, 0.35 AI, and an increase in propene yield of 3.2 wt % at 74% conversion as compared to Ecat alone. The 50% additive (A-50), when subjected to the above tests, show a 0.52 AI, and an increase in propene yield of about 4 wt % at 74% conversion as compared to Ecat alone. In comparison to the examples below, it is shown that one can maintain similar physicals and better performance as more zeolite is added through the use of the inventions as described herein.

Example 1. Six additive samples were made used the methodology described herein. The amount of zeolite in the samples was maintained at 50% to compare the benefits of the invention over the current state of the art. The LCA used in this and the following examples had a crystallite size of about 25-30 nm. The SCA used in this and the following examples had crystallite size of about 4-5 nm. The six samples had the following formulations:

TABLE 1

|  | Cat 1-1 | Cat 1-2 | Cat 1-3 | Cat 1-4 | Cat 1-5 | Cat 1-6 |
| --- | --- | --- | --- | --- | --- | --- |
| ZSM-5 | 50% | 50% | 50% | 50% | 50% | 50% |
| SCA | 3% | 3.80% | 4.50% | 3% | 3.80% | 4.50% |
| LCA | 8.50% | 7.70% | 7% | 8.50% | 7.70% | 7.00% |
| SiO$_2$ | 10% | 10% | 10% | 9.00% | 9.00% | 9.00% |
| P$_2$O$_5$ | 10.50% | 10.50% | 10.50% | 11.30% | 11.30% | 11.30% |
| AI_LA 600 C. | 0.6 | 0.38 | 0.28 | 0.36 | 0.32 | 0.18 |
| Inc/Dec Wt % Propylene from A-50* | equivalent* | equivalent* | equivalent* | equivalent* | equivalent* | equivalent* |

*Equivalent within the error of the test compared to A-50

The six additives were then performance tested to determine physical properties according to the test procedures set forth above. In this example, it is shown that it is possible to make an additive with sufficient performance and better physicals with a dual source alumina. As can be seen from the results from above, with the same zeolite content it is possible to make a catalyst with improved attrition and similar if not improved propylene production.

Example 2. In this set of examples, the zeolite total was raised to 60%. It is therefore expected that there would be an increase in propylene production but that there would also be some loss of attrition. However, as the results indicate, it is possible to maintain strong physical properties in a 60% zeolite catalyst. Example 2 utilizes the same alumina sources as Example 1.

TABLE 2

|  | Cat 2-1 | Cat 2-2 | Cat 2-3 | Cat 2-4 | Cat 2-5 | Cat 2-6 |
| --- | --- | --- | --- | --- | --- | --- |
| ZSM-5 | 60.0% | 60.0% | 60.0% | 60.0% | 60.0% | 60.0% |
| SiO$_2$ | 5.0% | 5.0% | 5.0% | 5.0% | 5.0% | 5.0% |
| LCA | 7.5% | 7.5% | 7.5% | 7.0% | 7.0% | 6.5% |
| SCA | 4.0% | 4.0% | 4.0% | 4.5% | 4.5% | 5.0% |
| P$_2$O$_5$ | 11.5% | 12.5% | 13.5% | 11.5% | 12.5% | 12.5% |
| AI_LA 600 C. | 0.36 | 0.43 | 0.44 | 0.49 | 0.34 | 0.33 |
| Inc/Dec Wt % Propylene from A-50 | +0.64 | +0.85 | +0.59 | +0.65 | +0.62 | +0.65 |

Example 3. In this example, it is examined the ratio of SCA to LCA with varied P$_2$O$_5$ content. All samples in this set contain about 5 wt % silica sol. This data shows that you can have the same percentage of SCA in the sample but the amount of added P$_2$O$_5$ will have an effect on the performance. Comparing Examples 3-3 and 3-5, one finds that the propene yield for the 50% ZSM-5 additive is 1 wt % higher in example 3-5 due to optimized P$_2$O$_5$ to SCA ratio. Further, it appears that a wt ratio of P$_2$O$_5$ to SCA is preferably above 1.7. Example 3 utilizes the same alumina sources as Example 1.

TABLE 3

|  | Cat 3-1 | Cat 3-2 | Cat 3-3 | Cat 3-4 | Cat 3-5 |
| --- | --- | --- | --- | --- | --- |
| ZSM-5 | 50 | 50 | 50 | 50 | 50 |
| SCA | 6.6 | 5.6 | 6.6 | 4.6 | 4.6 |
| LCA | 4.9 | 5.9 | 4.9 | 6.9 | 6.9 |
| RATIO LCA/HCA | 1.35 | 0.95 | 1.35 | 0.67 | 0.67 |
| P$_2$O$_5$ WT% | 12.5 | 11.5 | 10.5 | 12.5 | 10.5 |
| inc/dec from A-40 | +0.5 | +0.4 | -0.3 | +0.75 | +0.75 |
| AI_LA 600 C. | 0.17 | 0.14 | 0.16 | 0.3 | 0.3 |

Example 4. In this example, it is examined the use of Gibbsite as the source of the large crystallite alumina. The gibbsite is first milled to preferably below 2 microns prior to its introduction. The following results show better physicals and equal performance when the balance of SCA and LCA are matched to the total P$_2$O$_5$ content when compared to a commercial additive with 50% ZSM-5. The LCA used in this and the following examples had a crystallite size of about 235 nm. The SCA used in this and the following examples had a crystallite size of about 4-5 nm.

TABLE 4

|  | Cat 4-1 | Cat 4-2 | Cat 4-3 |
| --- | --- | --- | --- |
| ZSM-5 | 50% | 50% | 50% |
| SCA | 3.80% | 4.50% | 6.00% |

TABLE 4-continued

|  | Cat 4-1 | Cat 4-2 | Cat 4-3 |
| --- | --- | --- | --- |
| gibbsite | 7.70% | 7.00% | 5.50% |
| SiO$_2$ | 8 | 8 | 8 |
| P$_2$O$_5$ | 12% | 12% | 12% |
| Al_LA 600 C. | 0.2 | 0.22 | 0.17 |
| Inc/Dec Wt % Propylene from A-50 | −0.3 | −1.4 | −2.0 |

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise. This invention is susceptible to considerable variation in its practice. Therefore the foregoing description is not intended to limit, and should not be construed as limiting, the invention to the particular exemplifications presented hereinabove.

The invention claimed is:

1. An FCC additive composition comprising:
   a. about 35 wt % to about 80 wt % zeolite;
   b. about 0 wt % to about 10 wt % of silica binder;
   c. about 7 wt % to about 20 wt % P$_2$O$_5$;
   d. about 10.5 wt % to about 20 wt % alumina that comprises at least one large crystallite alumina having an average crystallite size of about 25 nm or greater and at least one small crystallite alumina having an average crystallite size from about 4 nm to about 5 nm;
   e. the balance clay.

2. The additive of claim 1 wherein the zeolite is selected from the group consisting of MFI-type zeolites, MEL-type zeolites, MTW-type zeolites, MWW-type zeolites, MCM-36, MCM-49, MCM-56, and BEA-type zeolites or mixtures thereof.

3. The additive of claim 2 wherein the zeolite is MFI-type zeolite.

4. The additive of claim 3 wherein the zeolite is ZSM-5.

5. The additive of claim 1 wherein a source of P$_2$O$_5$ is selected from the group consisting of phosphoric acid, ammonium dihydrogen phosphate, diammonium hydrogen phosphate, ammonium hypophosphate, ammonium orthophosphate, ammonium dihydrogen orthophosphate, ammonium hydrogen orthophosphate, triammonium phosphate, phosphines, and phosphites and mixtures thereof.

6. The additive of claim 1 wherein the at least one large crystallite size alumina is in an amount of greater than 0 to about 10 wt %.

7. The additive of claim 1 wherein the at least one small crystallite size alumina is in an amount of about 2.5 to about 15 wt %.

8. The additive of claim 1 wherein the source of the at least one large crystallite size alumina comprises boehmite.

9. The additive of claim 1 wherein the source of the at least one small crystallite size alumina comprises either pseudo-boehmite or alumina sols.

10. The additive of claim 1 wherein the alumina source comprises at least one non-boehmite alumina and at least one small crystallite alumina.

11. The additive of claim 10 wherein the at least one small crystallite size alumina is in an amount of about 2.5 to about 15 wt %.

12. The additive of claim 10 wherein the at least one non-boehmite alumina is in an amount of greater than 0 to about 10 wt %.

13. The additive of claim 10 wherein the at least one non-boehmite is gibbsite.

14. An FCC additive composition comprising:
   a. about 35 wt % to about 80 wt % zeolite;
   b. about 0 wt % to about 10 wt % of silica binder;
   c. about 7 wt % to about 20 wt % P$_2$O$_5$;
   d. about 10.5 wt % to about 20 wt % alumina that comprises two different sources of alumina comprising at least one large crystallite alumina having an average crystallite size of about 25 nm or greater and at least one small crystallite alumina having an average crystallite size from about 4 nm to about 5 nm;
   e. the balance clay;
wherein the ratio of the P$_2$O$_5$ to the at least one small crystallite alumina is greater than about 1.7.

* * * * *